United States Patent [19]

Baldwin et al.

[11] Patent Number: 4,871,739
[45] Date of Patent: Oct. 3, 1989

[54] SUBSTITUTED 6H-7,8-DIHYDROTHIAPYRANO(3,2-D)-PYRIMIDINES AS HYOPGLYCEMIC AGENTS

[75] Inventors: John J. Baldwin, Gwynedd Valley, Pa.; Richard L. Tolman, Warren, N.J.; Mu T. Wu, Clark, N.J.

[73] Assignee: Merck & Co., Inc., Rahway, N.J.

[21] Appl. No.: 5,720

[22] Filed: Jan. 21, 1987

[51] Int. Cl.$^4$ ................ C07D 495/04; A61K 31/505; A61K 31/535
[52] U.S. Cl. .................................... 514/254; 544/278; 544/117; 514/258; 514/236.2; 546/244
[58] Field of Search ................ 514/258, 254; 544/278

[56] References Cited

U.S. PATENT DOCUMENTS

| | | | |
|---|---|---|---|
| 3,272,811 | 9/1966 | Ohnacker et al. | 544/278 |
| 3,318,881 | 5/1967 | Ohnacker et al. | 544/278 |
| 3,318,883 | 5/1967 | Ohnacker et al. | 544/278 |
| 4,435,566 | 3/1984 | Ohno et al. | 544/278 |

FOREIGN PATENT DOCUMENTS

| | | |
|---|---|---|
| 724745 | 5/1969 | Belgium . |
| 1593867 | 7/1970 | France . |
| 2119368 | 11/1983 | United Kingdom . |

OTHER PUBLICATIONS

Ohno et al. II, *Chem. Pharm. Bull.* 34, pp. 4150-4165, (Oct., 1986).
DeGraw et al. *Journal of Heterocyclic Chemistry* 23 1-4 (1986).
Allinger et al. *Organic Chemistry,* Warth Publishers Inc. New York, New York, pp. 339-341 (1971).
Fieser and Fieser *Advanced Organic Chemistry* Reinhold Publishing Co. New York, New York, pp. 213-218 (1961).

*Primary Examiner*—Mukund J. Shah
*Assistant Examiner*—E. Bernhardt
*Attorney, Agent, or Firm*—David L. Rose; Hesna J. Pfeiffer

[57] ABSTRACT

There are disclosed certain 2-substituted-4-substituted 6H-7,8-dihydrothiapyrano[3,2-d]pyrimidines which have oral hypoglycemic activity and with such ability to lower blood sugar are useful in the treatment of type II diabetes and/or obesity with associated insulin resistance. Processes for the preparation of such compounds and compositions containing such compounds as the active ingredient thereof are also disclosed. The compounds are also β-adrenergic blocking agonists or α-adrenergic blocking agents and act as ocular antihypertensives and are useful for the treatment of glaucoma and other eye disorders.

7 Claims, No Drawings

SUBSTITUTED 6H-7,8-DIHYDROTHIAPYRANO(3,2-D)-PYRIMIDINES AS HYOPGLYCEMIC AGENTS

BACKGROUND OF THE INVENTION

Certain 6H-7,8-dihydrothiapyrano[3,2-d]pyrimidines are disclosed in Belgian Pat. No. 724745 as intermediates for the preparation of compounds with cardiovascular and coronary dilation activity, however, suggestion is made neither of any hypoglycemic activity nor of weight reducing properties for either the intermediates or the final products. Great Britain No. 2119368 discloses 6H-7,8-dihydrothiapyrano[3,2-d]pyrimidines with a very different substitution pattern on the nucleus when compared with the instant compounds. U.S. Pat. Nos. 3,318,883, 3,272,811, and 3,318,881 disclose dihydrothieno[3,2-d]pyrimidines which differ from the instant compounds in having a 5-membered heteroaromatic sulfur-containing ring rather than a saturated 6-membered ring.

SUMMARY OF THE INVENTION

The instant invention is concerned with novel 6H-7,8-dihydrothiapyrano[3,2-d]pyrimidines which are useful as hypoglycemic and/or weight reducing agents. These compounds are also β-adrenergic blocking agonists and α-adrenergic blocking agents and are also useful as ocular antihypertensives and in the treatment of glaucoma and other eye disorders. Thus, it is an object of this invention to describe such compounds. It is a further object of this invention to describe the hypoglycemic activity of such compounds. A still further object is to describe compositions containing such compounds as the active ingredient thereof. Further objects will become apparent from a reading of the following description.

DESCRIPTION OF THE INVENTION

The 2-substituted-4-substituted 6H-7,8-dihydrothiapyrano[3,2-d]pyrimidines of this invention are novel compounds with significant hypoglycemic activity. The compounds have the following structure:

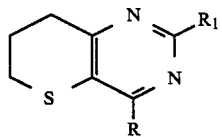

wherein:
$R_1$ is hydrogen, loweralkyl, loweralkenyl of from 2 to 6 carbon atoms, cycloalkyl of from 3 to 6 carbon atoms, phenyl, nitrophenyl, pyridyl, phenylloweralkyl, loweralkoxy, loweralkylthio, loweralkoxyloweralkyl or phenylloweralkoxyloweralkyl;
R is

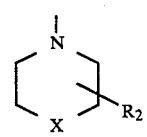

wherein $R_2$ is hydrogen or lower alkyl; X is —CH(NH$_2$), —(C=NOH)—, —(C=NOAlk)— where alk is loweralkyl or —(N—R$_3$)— where R$_3$ is loweralkenyl of from 2 to 6 carbon atoms, loweralkynyl of from 2 to 6 carbon atoms, cycloalkyl of from 3 to 6 carbon atoms, hydroxyloweralkyl, formyl, loweralkoxycarbonyl or phenylloweralkyl; and $R_3$ can also be loweralkyl provided that $R_1$ is not simultaneously hydrogen or loweralkyl at the same time; or R is
hydrogen or loweralkyl and $R_1$ is morpholino, piperidino, 4-hydroxyiminopiperidino, loweralkoxyiminopiperidino, 4-aminopiperidino, piperazino, N-loweralkylpiperazino or N-hydroxyloweralkylpiperazino.

The loweralkyl group of this invention may contain from 1 to 10 carbon atoms and may be in either a straight or branched configuration. Exemplary of such groups are methyl, ethyl, propyl, isopropyl, butyl, sec-butyl, pentyl, hexyl, heptyl, octyl, nonyl, decyl, and the like.

The term "halogen" or "halo" is intended to include those halogens selected from fluorine, chlorine, bromine or iodine.

The preferred compounds of this invention are those wherein $R_1$ is ethyl, n-propyl, cyclopropyl, vinyl, or 2-hydroxyethyl; X is N—R$_3$ where R$_3$ is lower alkenyl or hydroxy lower alkyl. Further preferred embodiments are realized when $R_3$ is 2-propenyl or 2-hydroxyethyl.

The instant compounds are prepared from the appropriate $R_1$-substituted thiapyranopyrimidin-4-one which is treated with phosphorus oxychloride to prepare the analogous 4-chloro compound which, with treatment with the appropriately substituted amine or heterocyclic amine prepares the desired compounds as outlined in the following reaction scheme:

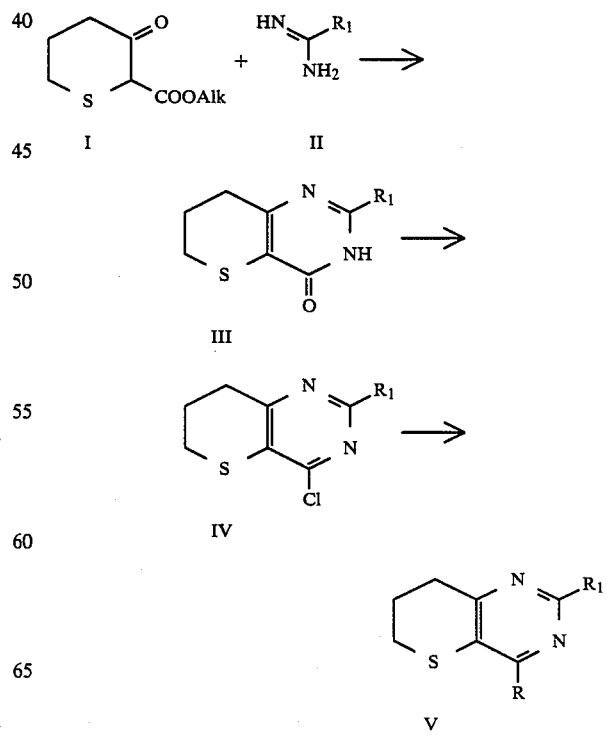

wherein R and $R_1$ are as defined above and Alk is loweralkyl.

In the first step of the above reaction scheme, a 2-carbalkoxy-3-oxotetrahydrothiapyran (I) is reacted with an $R_1$-substituted amidine (II). The free base of the amidine is usually employed which is generally generated in situ by treating an amidine salt with a strong base. While any base that is a stronger base than the amidine itself may be used, generally an alkali metal base, such as sodium or potassium alkoxide is preferred. The solvent is generally a solvent compatible with the base and it is thus generally preferred to use an alcohol which corresponds to the alkoxide base used, such as methanol or ethanol. Sodium methoxide in methanol is the preferred solvent system and base. The amidine free base is then combined with compound I to prepare the 2-$R_1$-substituted-7,8-dihydro-6H-thiapyrano[3,2-d]pyrimidine-4-one (III). The reaction is carried out at from 0° C. to the reflux temperature of the reaction mixture and is generally complete in from 30 minutes to 24 hours. It is preferred to carry out the reaction at about room temperature. The product is isolated using techniques known to those skilled in the art with the product generally not being purified but rather used directly in the next step.

The 2-$R_1$-substituted-7,8-dihydro-6H-thiapyrano[3,2-d]pyrimidine-4-one (III) is then reacted with a chlorinating agent such as phosphorus oxychloride, thionyl chloride and the like. While a solvent may be employed it is generally preferred to use the chlorinating agent in excess and to dispense with the use of a solvent. Generally the reaction is heated to at least 50° C. up to the reflux temperature of the reaction mixture for from about 3 hours to 3 days. It is preferred to use phosphorus oxychloride as the chlorinating agent and to heat it at about 100° C. overnight. The chlorinated compound (IV) is isolated using known techniques.

The 2-$R_1$-4-R-substituted-7,8-dihydro6H-thiapyrano[3,2-d]pyrimidine compounds (V) are prepared from the 4-chloro compounds (IV) by displacing the chlorine with the appropriate cyclo amine.

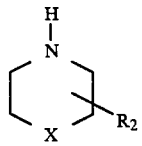

The reaction may be carried out neat, however, preferably the reaction is carried out in an unreactive alcohol solvent although any solvent which does not react with compound IV or the amine is suitable such as ethers, THF, DMF, benzene, and the like. The reaction is carried out at elevated temperatures of from 80° to 150° C. and is generally complete in from 3 to 24 hours. It is preferred to heat the reaction at from 100°-120° C. in an alcohol solvent with a boiling point in excess of the reaction temperature. Thus, isoamyl alcohol with a boiling point of 132° C. is a preferred solvent.

Generally the amine reactant is used in excess with at least 2 and preferably 3 or more molar equivalents in order to provide a scavenger for the hydrogen chloride liberated during the course of the reaction. Alternatively, where the amine reactant is difficult to obtain or costly, a single molar equivalent may be used along with a tertiary amine such as triethylamine or pyridine to act as the scavenger for the hydrogen chloride. The products are purified using standard techniques, and are preferably isolated as the acid addition or other physiologically acceptable salt such as the hydrochloride, nitrate, sulfate, maleate, citrate, and the like.

Those compounds wherein R is hydrogen or loweralkyl and $R_1$ is morpholino, piperazino, or N-loweralkylpiperazino are prepared from 2,4-dichloro-7,8-dihydro-6H-thiapyrano[3,2-d]pyrimidine, a known compound. (See UK patent application Ser. No. 2119368A) When R is hydrogen, the 4-chloro group is selectively removed by hydrogenation, such as catalytic hydrogenation with a platinum group metal such as platinum, palladium, rhodium, osmium, and the like, preferably supported on an inert carrier, such as carbon. Standard hydrogenation techniques are employed and the reaction is complete in from ½ to 8 hours. Hydrogen at from 1 to 4 atmospheres (gauge) is employed and the reaction is carried out in a solvent inert to hydrogenation and the catalyst such as a lower alcohol. Room temperature is preferred, however, elevated temperature of up to 50° C. may be employed. The product is isolated using standard techniques.

When R is loweralkyl, the dichloro compound is treated with an alkylating agent such as loweralkyltriphenyl phosphonium bromide. The reaction is carried out in a dry inert solvent such as dimethoxy ethane under a blanket of an inert gas, such as nitrogen, with a reaction promoter such as n-butyl lithium. The reaction is complete in from 1 to 4 hours at an initial temperature from −50° C. to 0° C. followed by a reaction temperature of from 0° to 50° C., preferably room temperature.

The following reaction scheme outlines the complete process:

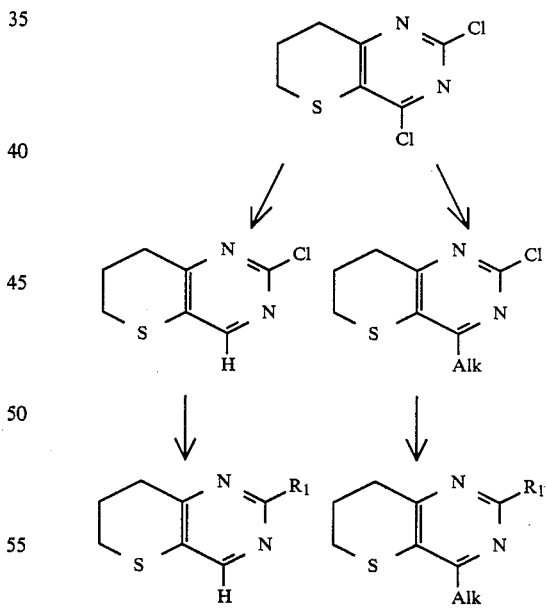

The monochloro compound is reacted with morpholine, piperazine, N-loweralkylpiperazine or a piperazine protected with acyl or BOC protecting groups in the same manner as described above for displacing the chlorine for the 4-position group with a heterocyclic base.

Diabetes is a condition characterized by abnormal insulin secretion and a variety of metabolic and vascular manifestations reflected in a tendency toward inappropriately elevated blood glucose levels and which if left poorly treated or untreated can result in accelerated, nonspecific atherosclerosis, neuropathy and thickened capillary lamina causing renal and retinal impairment. Diabetes is characterized as being insulin dependent (Type I) and non-insulin dependent (Type II). Type I diabetes is due to damage and eventual loss of the β-cells of the pancreatic islets of Langerhans with a resulting loss of insulin production. Type II diabetics secrete insulin, however, the insulin is somehow not properly or effectively utilized in the metabolism of blood sugars and glucose accumulates in the blood to above normal levels. This condition is termed insulin resistance.

With the certainty of serious complications resulting from high glucose levels in poorly controlled or uncontrolled diabetics, means to lower blood glucose have been research goals for a considerable period of time. With Type I diabetes glucose control can only be achieved with daily insulin injections. With Type II diabetes glucose control can be effected from a combination of diet and drugs which lower glucose levels. The currently available oral hypoglycemic agents are not completely satisfactory since they may not offer complete blood glucose control or may provide a variety of undesirable side effects or they may elevate insulin concentrations to undesirable and dangerous levels. Thus, the search for improved oral hypoglycemic agents is a continuing one.

As previously indicated, the compounds of this invention are all readily adapted to therapeutic use as oral hypoglycemic agents in view of their ability to lower the blood sugar levels of diabetic subjects to a statistically significant degree. For instance, 2-methyl-4-[4-(2-propenyl)piperazinyl]thiapyrano[3,2-d]pyrimidine, a typical and preferred agent of the present invention, has been found to consistently lower blood sugar levels and improve glucose tolerance in either fasted or fed diabetic (i.e., hyperglycemic) mice to a statistically significant degree when given by the oral route of administration at dose levels ranging from 1 mg/kg to 100 mg/kg, respectively, without showing any toxic side effects. The compounds of the instant invention have an additional advantage in that they produce a hypoglycemic effect only in biological situations of high glucose concentration. The other compounds of this invention also produce similar results. In general, these compounds are ordinarily administered at dosage levels ranging from about 1 mg to about 500 mg per kg of body weight per day, although variations will necessarily occur depending upon the condition and individual response of the subject being treated and the particular type of oral pharmaceutical formulation chosen.

Administration over time to obese, insulin resistant mice, resulted in a significant reduction in body weight.

In connection with the use of the compounds of this invention for the treatment of diabetic subjects, it is to be noted that they may be administered either alone or in combination with pharmaceutically acceptable carriers and that such administration can be carried out in both single and multiple dosages. More particularly, the novel compounds of the invention can be administered in a wide variety of different dosage forms, i.e., they may be combined with various pharmaceutically acceptable inert carriers in the forms of tablets, capsules, lozenges, troches, hard candies, powders, aqueous suspension, elixirs, syrups and the like. Such carriers include diluents or fillers, sterile aqueous media and various non-toxic organic solvents, etc. Moreover, such oral pharmaceutical compositions can be suitably sweetened and/or flavored by means of various agents of the type commonly employed for just such a purpose. In general, the therapeutically-effective compounds of this invention are present in such dosage forms at concentration levels ranging from about 0.5% to about 90% by weight of the total composition, i.e., in amounts which are sufficient to provide the desired unit dosage.

For purposes of oral administration, tablets containing various excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include the high molecular weight polyethylene glycols. When aqueous suspensions and/or elixirs are desired for oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

The activity of the compounds of the present invention, as hypoglycemic agents, is determined by their ability to lower blood sugar levels in the fasted or fed genetically hyperglycemic mouse when tested therein for such purposes according to the procedures described by Saperstein et al. as submitted to the journal *Diabetes* and summarized as follows: Genetically obese mice (ob/ob) were fasted overnight. The compounds were administered orally via a stomach tube and each mouse serially bled from the orbital sinus at various times and the blood samples were analyzed for blood glucose. When the effects of the compounds on blood glucose levels were to be determined, glucose was administered orally at a rate of 2 g per kg. 30 minutes after administration of the test compound. Glucose in the blood was determined by the potassium ferricyanide potassium ferrocyanide oxidation reaction auto analyzer. The latter method measures directly the amount of glucose in the blood at any given time and from this, the maximum percent decrease in blood sugar can be readily calculated and reported as hypoglycemic activity per se. In this way, many of the present compounds are shown to markedly improve glucose tolerance of non-anesthetized hyperglycemic mice when administered to them at dose levels as low as 10 mg/kg orally and to lower fasting blood glucose levels when administered at dose levels as low as 30 mg/kg orally.

The β-adrenergic blocking properties of the novel compounds of this invention indicate that they are useful in the treatment of conditions such as ocular hypertension, hypertension, angina pectoris, or certain arrhythmias which are known to be amenable to treatment with β-adrenergic blocking agents.

For use as β-adrenergic blocking agents, the present compounds can be administered orally, transdermally, or parenterally; i.e., intravenously, interperitoneally, etc. and in any suitable dosage form. The compounds may be offered in a form (a) for oral administration; e.g., as tablets, in combination with other compounding ingredients customarily used such as talc, vegetable oils, polyols, benzyl alcohols, gums, gelatin, starches, and other carriers; as liquids dissolved or dispersed or emulsified in a suitable liquid carrier; in capsules encapsulated in a suitable encapsulating material; or (b) for parenteral administration dissolved or dispersed in a suitable liquid carrier such as solution or as an emulsion, or (c) as an aerosol or patch for transdermal administration. The ratio of active compound to compounding ingredients; i.e., carrier, diluent, etc., will vary as the dosage form requires. Generally, doses of the present compounds of from about 0.01 to about 50 mg/kg and perferably from about 0.1 to about 20 mg/kg of body weight per day may be used. Dosage may be single or multiple depending on the daily total required and the unit dosage.

A further embodiment of this invention is the method of treating elevated intraocular pressure by the topical ocular administration to a patient in need of such treatment of an effective intraocular pressure lowering amount of one of or a mixture of compounds of this invention.

A unit dose comprises about 0.001 to 5.0 mg, preferably about 0.005 to 2.0 mg, and especially about 0.05 to 1.0 mg of active compound per eye. Multiple unit doses are administered as needed to achieve and maintain a normotensive or close to normotensive ocular condition.

A still further embodiment of this invention is the novel ophthalmic formulations comprising one of the previously mentioned compounds as active ingredient. The ophthalmic composition of this invention may be in the form of a solution, suspension, ointment, gel or solid insert and contain about 0.01 to 5% and especially about 0.5 to 2% by weight of medicament. Higher concentrations as, for example about 10% or lower concentrations can be employed.

The pharmaceutical preparation which contains the compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600; carbowaxes 1,000, 1,500, 4,000, 6,000 and 10,000; antibacterial components such as quaternary ammonium compounds, phenylmercuric salts known to have cold sterilizing properties and which are non-injurious in use, thimerosal, methyl and propyl paraben, benzyl alcohol, phenyl ethanol; buffering ingredients such as sodium chloride, sodium borate, sodium acetates, gluconate buffers; and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a solid insert. For example, one may use a solid water soluble polymer as the carrier for the medicament. The polymer used to form the insert may be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates such as polyacrylic acid salts, ethylacrylates, polyacrylamides; natural products such as gelatin, alginates, pectins, tragacanth, karaya, chondrus, agar, acacia; the starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, and mixtures of said polymers. The instant invention is further described by the following examples which are intended to be merely descriptive and should not be construed as limitative of the invention.

EXAMPLE 1

General Procedure I

An amidine hydrochloride was added to an equivalent amount of 1.5–2N sodium methoxide in methanol. After 5–10 minutes when sodium chloride precipitation was complete the solution of amidine was filtered directly into an equivalent of 2-carbethoxy-3-oxotetrahydrothiapyran (E. A. Fehnel, *J. Amer. Chem. Soc.* 74, 1569 (1952)) that may or may not be dissolved in a small amount of methanol. In general the concentration of reagents in the final reaction mixture ranges from 1–2 mmoles/ml of methanol. The product usually begins to precipitate after an hour or two. After the reaction mixture was allowed to stand overnight, the product was isolated by filtration. An additional crop of product was sometimes obtained by concentration of the mother liquors. The product is usually sufficiently pure for use in the next step. Should recrystallization be necessary, methanol is the appropriate solvent.

EXAMPLE 2

General Procedure II

A 2-substituted-7,8-dihydro-6H-thiapyrano[3,2-d]pyrimidin-4-one was suspended in phosphorus oxychloride. The concentration of the suspension ranges from 1 g/10 ml to 1 g/5 ml and is preferentially at 1 g/5 ml. The mixture is stirred and heated to reflux (On some occasions, 2 ml of N,N-diethylaniline per gram of pyrimidinone is added). The mixture becomes homogeneous within several hours, but heating is continued for a total of six to eighteen hours. After the mixture has been allowed to cool to room temperature it is poured slowly onto excess ice and water with vigorous agitation and a solvent such as chloroform or methylene chloride is added. It is important to keep the temperature low during hydrolysis and the subsequent neutralization reaction. After the hydrolysis mixture was made alkaline with 10N sodium hydroxide, the product was extracted into chloroform or methylene chloride. The organic extract was washed with saturated brine, dried over anhydrous magnesium sulfate, and concentrated to dryness under reduced pressure. It is usually expedient to remove impurities from the product by chromatography on silica gel (E. Merck Kieselgel 60 (70–230 mesh ASTM)). Elution was accomplished with 2% methanol in chloroform or cyclohexane-ethyl acetate (5:1). Concentration of the product-containing fractions to dryness under reduced pressure yields the pure product.

EXAMPLE 3
Procedure III

Amination of the chloroheterocycle of Procedure II was accomplished with N-formylpiperazine, N-t-butyloxycarbonylpiperazine, piperazine, 1-methylpiperazine, or several other appropriate amines.

A. With N-formylpiperazine(piperazine-1-carboxaldehyde)

A solution (1 mmole/3 ml) of chloroheterocycle from Procedure II in benzene was stirred while 4 equivalents of piperazine-1-carboxyaldehyde was added. The mixture was stirred and heated under reflux for about six to eight hours. After the mixture had cooled to room temperature it was filtered, and the benzene phase was concentrated to dryness. The residue was purified by chromatography on silica gel using 2–4% methanol in chloroform for elution. Concentration of product-containing fractions to dryness under reduced pressure yields product that usually will crystallize on standing. Deformylation of the product is carried out according to Procedure IV.

Alternatively, the displacement reaction was run in isoamyl alcohol at 100° C. for 12–18 hours. When the reaction was complete, the mixture was concentrated to dryness under reduced pressure and the residue was partitioned between the components of a chloroform-water system at pH 10–11. The product was purified by chromatography on silica gel using 2% methanol in chloroform for elution.

B. With N-t-butyloxycarbonylpiperazine

A solution (1 mmole/4 ml) of chloroheterocycle from Procedure II in isoamyl alcohol was added dropwise in the course of about one hour to a solution (1 mmole/4 ml) of N-t-butyloxycarbonylpiperazine in isoamyl alcohol at 100°–120° C. The reaction mixture is monitored for disappearance of chloroheterocycle by thin layer chromatography. The reaction is usually complete within several hours. After a reaction time of 4–18 hours the reaction mixture was concentrated to dryness under reduced pressure and the residue was partitioned between chloroform and water after the pH was adjusted to 10–11 with sodium hydroxide. The product is purified by chromatography on silica gel using cyclohexane-ethyl acetate (5:1) for elution. Concentration of product-containing fractions to dryness under reduced pressure yields the compound in sufficient purity for deblocking of the piperazine moiety according to Procedure V.

C. With Piperazine or 1-Methylpiperazine (i) In Benzene: A solution (1 mmole/3 ml) of chloroheterocycle from Procedure II in benzene was mixed with a four-fold molar excess of piperazine in benzene (1 mmole/ml) and the reaction mixture was heated to reflux. Within an hour piperazine hydrochloride began to precipitate. The reaction was monitored by tlc for disappearance of starting chloroheterocycle. After a period of 4–18 hours, the reaction mixture was filtered and the benzene phase was concentrated to dryness. The residue was taken up in a chloroform-water system in which the pH was adjusted to 10–11 with sodium hydroxide. The chloroform extract was washed with saturated brine, dried over anhydrous magnesium sulfate and concentrated by dryness under reduced pressure. The product is usually sufficiently pure for conversion to the mono- or dihydrochloride with a slight excess of 2N hydrochloric acid or anhydrous hydrogen chloride in ethanol. The salt is finally crystallized from ethanol or ethanol-ether mixtures. (ii) In Isoamyl Alcohol: A solution (1 mmole/4 ml) of chloroheterocycle from Procedure II was added dropwise in the course of about one hour to a fourfold molar excess of piperazine or 1-methylpiperazine in isoamyl alcohol (1 mmole/5 ml) at 100°–120° C. The reaction was monitored for disappearance of starting chloroheterocycle by tlc. After a period of 4–18 hours, the reaction mixture was concentrated under reduced pressure, and the residue was partitioned between a chloroform-water system in which the pH was adjusted to 10–11 with sodium hydroxide. Concentration of the chloroform extract to dryness under reduced pressure gave a product that was purified by chromatography on silica gel using 5% methanol in chloroform for elution. Concentration of the product-containing fractions under reduced pressure gave material that was converted to the mono- or dihydrochloride salt with either a slight excess of 2N HCl or anhydrous hydrogen chloride in ethanol. The salt was crystallized from ethanol or ethanol-ether mixtures.

EXAMPLE 4
Procedure IV-Deformylation

The N-formylated product of Procedure III was dissolved in 2N hydrochloric acid at a concentration of about 25 mg/ml and the solution was heated to 90° C. for an hour. The solution was concentrated to dryness under reduced pressure. The residue was taken up in water and the solution was concentrated to dryness under reduced pressure. The dissolution and concentration process was repeated several times. Finally, the salt was crystallized from ethanol.

EXAMPLE 5
Procedure V-De-t-Butyloxycarbonylation

The N-t-butyloxycarbonyl compound of Procedure III was dissolved in trifluoroacetic acid at a concentration of 1 mmole/7 ml. After about one hour the reaction mixture was concentrated to dryness at room temperature. The product in aqueous solution was passed through a column of Dowex-1 ion exchange resin on the hydroxide ion cycle. After the aqueous solution was concentrated to dryness, the residue was converted to the mono- or dihydrochloride salt with a slight excess of 2N HCl; or hydrogen chloride in ethanol. The product was crystallized from ethanol or ethanol-ether.

Alternatively, the residue from evaporation of the trifluoroacetic acid reaction may be partitioned between the phases of a chloroform-water system after the pH was adjusted to 10–11 with sodium hydroxide rather than passing the residue through the ion-exchange column. The residue from the washed and dried chloroform extract is then coverted to the hydrochloride salt in the usual manner.

EXAMPLE 6

2-Cyclopropyl-4-(1-piperazinyl)-7,8-dihydro-6H-thiapyrano[3,2-d]pyrimidine Dihydrochloride

A.
2-Cyclopropyl-7,8-dihydro-6H-thiapyrano[3,2-d]pyrimidin-4-one

Cyclopropylcarboxamidine hydrochloride was converted to the title compound according to Procedure I. The crystalline product was obtained in 66% yield and showed an m/e of 208. The 200 MHz pmr spectrum of the product was fully compatible with the assigned structure.

Anal. Calcd for $C_{10}H_{12}N_2OS$ (208.28): N, 13.45; C, 57.66; H, 5.81; S, 15.39. Found: N, 13.49; C, 57.80; H, 5.78; S, 15.50.

B.
2-Cyclopropyl-4-chloro-7,8-dihydro-6H-thiapyrano[3,2-d]pyrimidine

The product of Step A was converted to the title compound according to Procedure II. For this case the 4-chloro analog crystallized directly from the reaction medium in 95% yield and was washed with ether. The product showed m/e=225 and a 200 MHz pmr spectrum was fully consistent with the proposed structure.

Anal. Calcd for $C_{10}H_{11}N_2SCl\cdot 0.37HCl$ (240.11): N, 11.67; C, 50.00; H, 4.77; Cl, 20.23; S, 13.36. Found: N, 11.57; C, 49.68; H, 4.76; Cl, 20.78; S, 13.56.

C.
2-Cyclopropyl-4-(1-piperazinyl)-7,8-dihydro-6H-thiapyrano[3,2-d]pyrimidine Dihydrochloride The product of step B was reacted with 4 equivalents of piperazine in isoamyl alcohol at 100° C. according to Procedure III. The product was converted to the dihydrochloride with anhydrous hydrogen chloride in ethanol. Crystallization of the product from hot ethanol gave the title compound in 38% yield. The product showed m/e=276 and a 200 MHz pmr spectrum was fully compatible with the designated structure.

Anal. Calcd for $C_{14}H_{22}Cl_2N_4S\cdot 0.6C_2H_5OH$ (376.96): N, 14.87; C, 48.43; H, 6.85; Cl, 18.81; S, 8.50. Found: N, 14.79; C, 47.96; H, 6.86; Cl, 17.57; S, 8.36.

EXAMPLE 7

2-Benzyl-4-(1-piperazinyl)-7,8-dihydro-6H-thiapyrano[3,2-d]pyrimidine Dihydrochloride

A.
2-Benzyl-7,8-dihydro-6H-thiapyrano-[3,2-d]pyrimidin-4-one

Phenylacetamidine hydrochloride was converted to the title compound according to the details of Procedure I. The crystalline product was isolated in 77% yield and showed m/e=258. The 200 MHz pmr spectrum of the product was completely compatible with the assigned structure of the product.

Anal. Calcd for $C_{14}H_{14}N_2OS$ (258.33): N. 10.85; C, 65.09; H, 5.46; S, 12.41. Found: N, 10.69; C, 64.88; H, 5.35; S, 12.24.

B.
2-Benzyl-4-chloro-7,8-dihydro-6H-thiapyrano[3,2-d]pyrimidine

The product of Step A was converted to the corresponding 4-chloro analog according to Procedure II. The title compound was obtained in 69% yield after purification by chromatography on silica gel using cyclohexane-ethyl acetate (3:1) for elution. The product showed m/e=276 and a 200 MHz pmr spectrum consistent with the projected structure.

Anal. Calcd for $C_{14}H_{13}ClN_2S$ (276.77): N, 10.12; C, 60.75; H, 4.73; Cl, 12.81; S, 11.58. Found: N, 10.26; C, 61.26; H, 4.87; Cl, 12.62; S, 11.27.

C.
2-Benzyl-4-(1-piperazinyl)-7,8-dihydro-6H-thiapyrano[3,2-d]pyrimidine Dihydrochloride The product of Step B was treated with four equivalents of piperazine in benzene according to Procedure III. The product was converted to the dihydrochloride without purification by chromatography and yielded the title compound in 66% yield after crystallization from ethanol. The product showed m/e=326 and a 200 MHz pmr spectrum full consistent with the assigned structure.

Anal. Calcd for $C_{18}H_{24}Cl_2N_4S$ (399.37): N, 14.03; C, 54.13; H, 6.06; Cl, 17.75; S, 8.03. Found: N, 14.10; C, 53.86; H, 6.25; Cl, 17.56; S, 7.76.

EXAMPLE 8

2-Phenyl-4-(1-piperazinyl)-7,8-dihydro-6H-thiapyrano[3,2-d]pyrimidine Dihydrochloride

A.
2-Phenyl-7,8-dihydro-6H-thiapyrano[3,2-d]pyrimidin-4-one

Benzamidine hydrochloride was converted to the title compound in 88% yield using the conditions of Procedure I. The product showed m/e=244 and a 200 MHz pmr spectrum consistent with the assigned structure.

Anal. Calcd for $C_{13}H_{12}N_2OS$ (244.30): N, 11.47; C, 63.91; H, 4.95; S, 13.12. Found: N, 11.29; C, 63.69; H, 5.01; S, 13.15.

B.
2-Phenyl-4-chloro-7,8-dihydro-6H-thiapyrano[3,2-d]pyrimidine

The product of Step A was reacted with phosphorus oxychloride according to Procedure II. The title compound was obtained in 95% yield and was sufficiently pure so as not to require chromatographic purification. (When this synthesis was run on scales larger than one gram, chromatography on silica gel using cyclohexane-ethyl acetate (3:1) was required and the yield slipped to 52%.) The product showed m/e=262 and a 200 MHz pmr spectrum fully in accord with the designated structure.

Anal. Calcd for $C_{13}H_{11}ClN_2S$ (262.76): N, 10.66; C, 59.42; H, 4.22; Cl, 13.50; S, 12.20. Found: N, 10.55; C, 59.29; H, 4.36; Cl, 13.53; S, 11.91.

C.
2-Phenyl-4-(4-formyl-1-piperazinyl)-7,8-dihydro-6H-thiapyrano[3,2-d]pyrimidine The product of Step B was reacted with four equivalents of piperazine-1-carboxyaldehyde in isoamyl alcohol at 100° C. according to Procedure III. The title compound was obtained in 38% yield after column chromatography using 2% methanol in chloroform followed by preparative thin layer chromatography on silica using the same eluant. The product showed m/e=340 and a 200 MHz pmr spectrum consistent with the proposed structure.

Anal. Calcd for $C_{18}H_{20}N_4OS$ (340.44): N, 16.46; C, 63.50; H, 5.92. Found: N, 16.37; C, 63.34; H, 5.88.

D.
2-Phenyl-4-(1-piperazinyl)-7,8-dihydro-6H-thiapyrano[3,2-d]pyrimidine Dihydrochloride The product of Step C was deformylated according to Procedure IV. The title compound was obtained in 77% yield after crystallization from ethanol and showed m/e=312. The 200 MHz pmr spectrum of the product is fully compatible with the designated structure.

Anal. Calcd for $C_{17}H_{22}Cl_2N_4S \cdot 81H_2O$ (399.94): N, 14.01; C, 51.05; H, 6.21; Cl, 17.73; S, 8.02. Found: N, 14.21; C, 50.62; H, 6.09; Cl, 17.53; S, 7.75.

EXAMPLE 9
2-Trichloromethyl-4-(1-piperazinyl)-7,8-dihydro-6H-thiapyrano[3,2-d]pyrimidine Dihydrochloride

A.
2-Trichloromethyl—7,8-dihydro-6H-thiapyrano[3,2-d]pyrimidin-4-one

Trichloroacetamidine (K. Dachlauer to I. G. Farbenind, Ger. Pat. No. 671,785, Feb. 14, 1939) is added to a solution (1.5 mmoles/ml) of an equivalent amount of 2-carboethoxy-3-oxotetrahydrothiapyran in ethanol. The mixture was allowed to stand overnight at room temperature. The product was isolated in 7% yield by filtration. (The low yield is apparently a result of the instability of the acetamidine which has a propensity to polymerize.) The product shows m/e=284, 286, 288 and a 200 MHz pmr spectrum consistent with the assigned structure.

Anal. Calcd for $C_8H_7Cl_3N_2OS$ (285.57): N, 9.81; C, 33.64; H, 2.47; Cl, 37.24; S, 11.23. Found: N, 9.67; C, 34.25; H, 2.75; Cl, 36.21; S, 10.12.

B.
2-Trichloromethyl-4-chloro-7,8-dihydro-6H-thiapyrano[3,2-d]pyrimidine The product of Step A was converted to the 4-chloro analog according to Procedure II. The product was purified by preparative thin layer chromatography on silica gel using cyclohexane-ethyl acetate (5:1) for development. The title compound was obtained in 45% yield. The product showed m/e=302, 304, 306 and a 200 MHz spectrum compatible with the assigned structure.

Anal. Calcd for $C_8H_6Cl_4N_2S$ (304.01): N, 9.22; C, 31.60; H, 1.99; S, 10.55; Cl, 46.64. Found: N, 9.23; C, 31.98; H, 2.11; S, 10.77; Cl, 45.36.

C.
2-Trichloromethyl-4-(4-t-butyloxycarbonyl-1-piperazinyl)-7,8-dihydro-6H-thiapyrano[3,2-d]pyrimidine The product of Step B was reacted with 4 equivalents of N-t-butyloxycarbonylpiperazine in isoamyl alcohol according to Procedure III. The product was purified by preparative thin layer chromatography on silica gel using cyclohexane-ethyl acetate (5:1) and yielded the title compound in 30–60% yield. The product showed m/e=452 and a 200 MHz pmr spectrum appropriate for the designated structure.

D.
2-Trichloromethyl-4-(1-piperazinyl)-7,8-dihydro-6H-thiapyrano[3,2-d]pyrimidine Monohydrochloride The product of Step C is converted to the title compound according to Procedure V using the alternative partition step rather than the ion-exchange procedure for generation of the free base form of the title compound. The product was obtained in about 25% yield. The product showed m/e=352, 354, 356 and a 200 MHz pmr spectrum consistent with the proposed structure.

Anal. Calcd for $C_{12}H_{16}Cl_4N_4S$ (390.16): N, 14.36; C, 36.94; H, 4.13. Found: N, 14.13; C, 37.27; H, 4.19.

EXAMPLE 10
2-Trifluoromethyl-4-(4-methyl-1-piperazinyl)-7,8-dihydro-6H-thiapyrano[3,2-d]pyrimidine Hydrochloride A solution of 4.5 g (40 mmoles) of trifluoroacetamidine (W. L. Reilley and H. C. Brown, *J. Amer. Chem. Soc.* 78, 6032 (1956). R. A. Moss, W. Guo, D. Z. Denney, K. N. Houk, and N, G. Rodan, *J. Amer. Chem. Soc.* 103, 6164 (1981)) in 15 ml of methanol was added to a solution of 7.6 g (40 mmoles) of ethyl 3-oxotetrahydrothiapyran-2-carboxylate in 15 ml of methanol. After being allowed to stand overnight, the solution was cooled and the wall of the vessel was "scratched" until the product precipitated. In this manner, 1.47 g of 2-trifluoromethyl-7,8-dihydro-6H-thiapyrano[3,2-d]pyrimidin-4-one was obtained by filtration.

A 0.7 g portion of the above pyrimidinone was converted to the corresponding 4-chloro analog according to procedure II. In this manner, 405 mg of 2-trifluoromethyl-4-chloro-7,8-dihydro-6H-thiapyrano[3,2-d]pyrimidine was obtained and used in the next step without further purification.

A solution of 200 mg (785 μmoles) of the above 4-chloro analog in 3 ml of isoamyl alcohol was treated with 315 mg of 1-methylpiperazine according to Procedure III. Purification of the product by preparative thin layer chromatography on silica using 5% methanol in chloroform yielded 198 mg of eluted product that was treated with 75 mg of anhydrous hydrogen chloride in 0.5 ml of ethanol. Crystallization of the product from ethanol yielded 154 mg of the title compound. The 200 MHz pmr spectrum is fully compatible with the projected structure and m/e=318 (calcd 318).

Anal. Calcd for $C_{13}H_{18}ClF_3N_4S$ (354.82): N, 15.79; C, 44.00; H, 5.11; Cl, 9.99; S, 9.04; F, 16.06. Found: N, 15.79; C, 44.29; H, 5.15; Cl, 9.88; S, 8.81; F, 14.74.

EXAMPLE 11
2-Methoxy-4-(4-methyl-1-piperazinyl)-7,8-dihydro-6H-thiapyrano[3,2-d]pyrimidine Dihydrochloride A solution of 570 mg (2 mmoles) of 2-chloro-4-(4-methyl-1-piperazinyl)-7,8-dihydro-6H-thiapyrano[3,2-d]pyrimidine (S. Ohno, et al. to Maruko Seiyaki Co., Ltd., U.K. patent application GB 2,117,368 A) in 7 ml of anhydrous dimethylformamide was treated with 540 mg (10 mmoles) of sodium methoxide and the mixture was stirred and heated at 125° C. for 18 hours. The mixture was concentrated to dryness under reduced pressure and the residue was partitioned between 50 ml of CHCl3 and 50 ml of H2O. The chloroform phase was separated and the aqueous phase was extracted with 50 ml of CHCl3. The combined chloroform extracts were washed with saturated brine, dried over anhydrous magnesium sulfate and concentrated to dryness under reduced pressure. The 570-mg residue was put on a 100 g (30 cm×5 cm (d)) column of silica gel and the product was eluted with 5% methanol in chloroform. The product which runs only slightly slower than the starting material on silica gel was isolated as "single-spot" pure material. After attempts to crystallize the product as a dimaleate salt failed the product was converted to the dihydrochloride with anhydrous hydrogen chloride in ethanol. The product was crystallized from ethanol-ether giving a 35% yield of title compound showing M+H=281 and a 200 MHz pmr spectrum fully compatible with the assigned structure.

Anal. Calcd for $C_{13}H_{22}Cl_2N_4OS \cdot 1H_2O$ (373.13): N, 15.01; C, 41.84; H, 6.54; Cl, 19.00; S, 8.59. Found: N, 14.91; C, 41.76; H, 6.23; Cl, 18.95; S, 7.73.

EXAMPLE 12

2-(β-Methoxyethyl)-4-(4-methyl-1-piperazinyl)-7,8-dihydro-6H-thiapyrano[3,2-d]pyrimidine Dihydrochloride

A.

2-(β-Methoxyethyl)-7,8-dihydro-6H-thiapyrano[3,2-d]pyrimidin-4-one

3-Methoxypropionamidine hydrochloride (2.77 g, 20 mmoles) in Procedure I yielded 2.6 of the title compound that showed m/e=226 (calcd 226) and a 200 MHz pmr spectrum fully compatible with the assigned structure.

Anal. Calcd for $C_{10}H_{14}N_2O_2S$ (226.29): N, 12.38; C, 53.08; H, 6.24; S, 14.17. Found: N, 12.48; C, 52.91; H, 6.28; S, 13.94.

B.

2-(β-Methoxyethyl)-4-chloro-7,8-dihydro-6H-thiapyrano[3,2-d]pyrimidine

Treatment of 1.2 g of the above pyrimidinone with phosphorus oxychloride according to Procedure II gave after chromatography, 584 mg of product showing m/e=244 (calcd 244) and a 200 MHz pmr spectrum fully in accord with its structure.

C.

2-(β-Methoxyethyl)-4-(4-methyl-1-piperazinyl)-7,8-dihydro-6H-thiapyrano[3,2-d]pyrimidine Dihydrochloride Treatment of 580 mg of the above 4-chloro intermediate in 9 ml of isoamyl alcohol with 920 mg of 1-methylpiperazine in 15 ml of isoamyl alcohol according to Procedure III yielded 480 mg of product after chromatography. Conversion of this product to the dihydrochloride on treatment with 100 mg of anhydrous hydrogen chloride in ethanol followed by crystallization of the product from ethanol-ether yielded 430 mg of the title compound showing a mass spectrum and a 200 MHz pmr spectrum fully in accord with the projected structure.

Anal. Calcd for $C_{15}H_{26}Cl_2N_4OS$ (381.36): N, 14.69; C, 47.24; H, 6.87; Cl, 18.59; S, 8.41. Found: N, 14.60; C, 46.95; H, 6.99; Cl, 16.89, 16.94; S, 8.11.

EXAMPLE 13

2-(β-Benzyloxyethyl)-4-(4-methyl-1-piperazinyl)-7,8-dihydro-6H-thiapyrano[3,2-d]pyrimidine Dihydrochloride

A.

2-(β-Benzyloxyethyl)-7,8-dihydro-6H-thiapyrano[3,2-d]pyrimidin-4-one

Treatment of 6.5 g of 3-benzyloxypropionamidine hydrochloride (Prepared in two steps from acrylonitrile, W. P. Untermohlen, Jr., *J. Amer. Chem. Soc.* 67, 1505 (1945). C. Djerassi and C. R. Scholz, to Ciba Pharm. Prod., U.S. Pat. No. 2,516,108, July 25, 1950.) with 5.7 g of ethyl 3-oxotetrahydrothiapyran-2-carboxylate according to Procedure I yielded 5.26 g of the title compound showing m/e=302 (calcd 302) and a 200 MHz pmr spectrum fully in accord with the projected structure.

Anal. Calcd for $C_{16}H_{18}N_2O_2S$ (302.40): N, 9.27; C, 63.55; H, 6.00; S, 10.60. Found: N, 9.23; C, 63.33; H, 6.04; S, 10.54.

B.

2-(β-Benzyloxyethyl)-4-(2,4,6-triisopropylbenzenesulfonyloxy)-7,8-dihydro-6H-thiapyrano[3,2-d]pyrimidine A solution of 3.02 g (10 mmoles) of the above pyrimidinone in 150 ml of methylene chloride was treated with 120 mg (1 mmole) of 4-dimethylaminopyridine 12.1 g (120 mmoles) of triethylamine and 4.54 g (15 mmoles) of 2,4,6-triisopropylbenzenesulfonyl chloride. After one hour the reaction mixture was concentrated to dryness and the residue was taken up in chloroform and plated onto 60 g of silica gel by evaporation under reduced pressure. The resulting adsorbent was added to the top of a 550 g column of silica gel packed in cyclohexane and the column was eluted with a 1:1 mixture of ethyl acetate and cyclohexane. In this manner 6.11 g of title product having a satisfactory 200 MHz pmr spectrum was isolated.

C.

2-(β-Benzyloxyethyl)-4-(4-methyl-1-piperazinyl)-7,8-dihydro-6H-thiapyrano[3,2-d]pyrimidine Dihydrochloride A solution of 2.07 g of the above 4-(2,4,6-triisopropylbenzenesulfonyloxy) analog (3.63 mmoles) and 1.82 g (18.15 mmoles) of 1-methylpiperazine in 35 ml of ethanol was heated at 50° C. overnight. The reaction mixture was concentrated to dryness under reduced pressure and the residue was partitioned between 100 ml of chloroform and 100 ml of water at pH 13. Concentration of the washed and dried chloroform extract to dryness yielded a 1.48 g residue that was purified by chromatography on silica gel using elution with 5% methanol in chloroform. The 200 MHz pmr spectrum of the free base form of the subject compound was fully in accord with the assigned structure.

Anal. Calcd for $C_{21}H_{28}N_4OS$ (384.53): N, 14.57; C, 65.59; H, 7.34; S, 8.34. Found: N, 14.70; C, 65.50; H, 7.37; S, 8.42.

A solution of 64 mg of the above free base in 2.5 ml of ethanol was treated with 15 mg of anhydrous hydrogen chloride in 0.1 ml of ethanol. After being concentrated to dryness, the residue was crystallized from 1.2 ml of hot ethanol to yield 38 mg of the subject compound that gave m/e=384 (calcd 384) and a satisfactory 200 MHz pmr spectrum.

Anal. Calcd for $C_{21}H_{30}Cl_2N_4OS$ (457.45): N, 12.25; C, 55.13; H, 6.61. Found: N, 12.07; C, 54.81; H, 6.63.

EXAMPLE 14

2-(β-Hydroxyethyl)-4-(4-methyl-1-piperazinyl)-7,8-dihydro-6H-thiapyrano[3,2-d]pyrimidine Dihydrochloride A solution of 149 mg (390 μmoles) of 2-(2-benzyloxyethyl)-4-(4-methyl-1-piperazinyl-7,8-dihydro-6H-thiapyrano[3,2-d]pyrimidine from Example 13 in 3 ml of trifluoroacetic acid was treated with 1.2 ml of 1M boron tris-trifluoroacetate in trifluoroacetic acid at ice bath temperature for one hour. After an additional hour of reaction at room temperature, the reaction mixture was evaporated to dryness. The residue showed some starting material remaining by tlc so that above treatment was repeated. The residue from the second treatment was taken up in a few ml of ethanol and treated with 0.5 ml of 5N NaOH. The mixture was concentrated at room temperature, diluted with water and extracted with chloroform. The chloroform soluble material which amounted to 88 mg was purified by preparative thin layer chromatography on a 500 μ 20×20 cm silica plate using 7.5% methanol in chloroform. A 43 mg fraction (Rf 0.3) was eluted and converted to the hydrochloride after treatment with 75 mg of anhydrous hydrogen chloride in ethanol. The product, isolated as a glass, showed M+H=295 (FAB) and a satisfactory 200 MHz pmr spectrum.

Anal. Calcd for $C_{14}H_{24}Cl_2N_4Os$ (366.73): N, 15.25; C, 45.77; H, 6.59. Found: N, 15.08; C, 45.90; H, 6.65.

EXAMPLE 15

2-Vinyl-4-(4-methyl-1-piperazinyl)-7,8-dihydro-6H-thiapyrano[3,2-d]pyrimidine Dihydrochloride A solution of 441 mg of 2-(β-hydroxyethyl)-4-(4-methyl-1-piperazinyl)-7,8-dihydro-6H-thiapyrano[3,2-d]pyrimidine in 10 ml of anhydrous methylene chloride was treated with 850 mg of methyltriphenoxyphosphonium iodide and the mixture was stirred at room temperature overnight.

The reaction mixture was diluted to a 50 ml volume with methylene chloride and the solution was washed with saturated aqueous sodium bicarbonate, dried over MgSO₄, filtered and concentrated to dryness. The residue (1.07 g) was purified by chromatography on a g silica gel column that was eluted first with chloroform and then 5% methanol in chloroform. The 310 mg of purified product was taken up in a few ml of ethanol and treated with 150 mg of anhydrous hydrogen chloride in ethanol. Crystallization of the product from 7 ml of hot ethanol yielded 260 mg of the title compound showing a satisfactory mass spectrum and 200 MHz pmr spectrum.

Anal. Calcd for $C_{14}H_{22}Cl_2N_4S$ (349.32): N, 16.04; C, 48.13; H, 6.35; Cl, 20.30; S, 9.18. Found: N, 16.10; C, 47.86; H, 6.24; Cl, 20.52; S, 9.04.

EXAMPLE 16

2-(Carboethoxymethyl)-4-(4-methyl-1-piperazinyl)-7,8-dihydro-6H-thiapyrano[3,2-d]pyrimidine

A.

2-(Carboethoxymethyl)-7,8-dihydro-6H-thiapyrano[3,2-d]pyrimidin-4-one

Treatment of 299 mg of ethyl amidinoacetate hydrochloride (D. J. Collins, *J. Chem. Soc.* 1337 (1963). Difficulty was experienced in getting reproducibly satisfactory preparations of this intermediate.) with 333 mg of ethyl 3-oxotetrahydrothiapyran-2-carboxylate by a modification of Procedure I in which ethanol was substituted for methanol gave a product which could not be crystallized so the reaction mixture was concentrated to dryness and the residue was triturated with ether. In this manner 314 mg of product was obtained and used directly in the next step. The mass spectrum and 200 MHz pmr spectrum of this product were satisfactory.

B.

2-(Carboethoxymethyl)-4-chloro-7,8-dihydro-6H-thiapyrano[3,2-d]pyrimidine

The product of Step A (314 mg) was treated with phosphorus oxychloride according to Procedure II. The 147 mg residue thus obtained was purified by preparative thin layer chromatography on two 20 cm×20 cm 1000 μ silica gel plates using a 1:1 cyclohexane-ethyl acetate system. In this manner, 52 mg of product showing Rf 0.51 was obtained. The mass spectrum and 200 MHz pmr spectrum were in accord with the projected structure of the title compound.

C.

2-(Carboethoxymethyl)-4-(4-methyl-1-piperazinyl)-7,8-dihydro-6H-thiapyrano[3,2-d]pyrimidine A solution of 113 mg of the product of Step B in 2.5 ml of isoamyl alcohol was treated with four equivalents of 1-methylpiperazine according to Procedure III. The 211 mg of product so obtained was purified by preparative thin layer chromatography on two 20 cm×20 cm 1000 μ silica gel plates using 5% methanol in chloroform. The 111 mg of product of Rf 0.40 showed a mass spectrum of 336 (calcd 336) and a 200 MHz pmr spectrum compatible with the projected structure.

EXAMPLE 17

2-Methyl-4-chloro-7,8-dihydro-6H-thiapyrano[3,2-d]pyrimidine

A.

2-Methyl-7,8-dihydro-6H-thiapyrano[3,2-d]pyrimidin-4-one (This compound and its synthesis is described by K. Thomae in French Patent 1,593,867, 10 July 1970.)

Acetamidine hydrochloride in Procedure I yielded the title compound in 79% yield. The crystalline product was obtained in two crops, the first melting at 224°–226° C. and the second at 223°–224° C. The 200 MHz pmr spectrum was fully in accord with the structure designated for the product. Similar syntheses gave a product showing:

m/e=182 and Anal. Calcd for $C_8H_{10}N_2OS$ (182.24): N, 15.38; C, 52.72; H, 5.53; S, 17.59. Found: N, 15.37; C, 52.76; H, 5.52; S, 17.68.

B.

2-Methyl-4-chloro-7,8-dihydro-6H-thiapyrano[3,2-d]pyrimidine (This compound and its synthesis are described by K. Thomae in French Pat. No. 1,593,867, 10 July 1970.)

The product of Step A was converted to the corresponding 4-chloro analog according to Procedure II. The product has been obtained in yields as high as 90% in small scale (e.g. 450 mg) reactions. Such products show m/e=200 and 200 MHz pmr spectra fully consistent with the designated structure.

Anal. Calcd for $C_8H_9ClN_2S$ (200.68): N, 13.96; C, 47.88; H, 4.52; Cl, 17.66; S, 15.98. Found: N, 14.16; C, 48.06; H, 4.48; Cl, 17.76; S, 16.02.

When the scale of the reaction was increased to several grams, it became necessary to purify the product by chromatography on silica gel using cyclohexane-ethyl acetate (1:1) for elution. Yields ranging from 70% to 30% have been realized as the scale of reaction increases. Temperature control at the quenching stage is apparently the critical factor in determining yield.

EXAMPLE 18

2-Methyl-4-(4-formyl-1-piperazinyl)-7,8-dihydro-6H-thiapyrano[3,2d]pyrimidine

The product of Example 17, Step B, was treated with four equivalents of N-formylpiperazine in benzene at 80° C. according to Procedure III. After the reaction mixture was filtered, the benzene phase was concentrated to dryness and the residue was purified by preparative thin layer chromatography on silica gel using 4% methanol in chloroform for development. The title product obtained in essentially quantitative yield showed m/e=278 and a 200 MHz pmr spectrum consistent with the designated structure of the product.

Anal. Calcd for $C_{13}H_{18}N_4OS$ (278.37): N, 20.13; C, 56.09; H, 6.52; S, 11.52. Found: N, 19.83; C, 55.84; H, 6.34; S, 11.25.

EXAMPLE 19

2-Methyl-4-(4-t-butylcarbonyl-1-piperazinyl)-7,8-dihydro-6H-thiapyrano[3,2-d]pyrimidine The product of Example 17, Step B, is reacted with four equivalents of N-t-butyloxycarbonylpiperazine in isoamyl alcohol at 100° C. as described in Procedure III.

EXAMPLE 20

2-Methyl-4-[4-(2-propenyl)-1-piperazinyl]-7,8-dihydro-6H-thiapyrano[3,2-d]pyrimidine Dihydrochloride The product of Example 17, Step B was treated with four equivalents of N-allylpiperazine (Prepared from piperazine monohydrate and allyl chloride according to Dahlbom, et al., *Acta Chemica Scandanavia* 15, 1367–1371 (1961) and references cited therein.) in isoamyl alcohol at 100° C. according to Procedure III. The product was purified by chromatography on silica gel using 5% methanol in chloroform as eluant. The product was converted to the dihydrochloride and crystallized from ethanol-ether. The crystalline product was dissolved in water and filtered through a pad of Super-Cel to remove insolubles and the clear aqueous solution was concentrated to dryness. The residue on crystallization from hot ethanol gave the pure title compound in 16% yield. The product showed M+H=291 (FAB mass spectrum) and gave 200 MHz pmr spectrum fully compatible with the assigned structure.

Anal. Calcd for $C_{15}H_{24}Cl_2N_4S \bullet 0.2C_2H_5OH \bullet 0.5$-$H_2O$ (381.56): N, 14.69; C, 48.47; H, 6.92; Cl, 18.58; S, 8.40. Found: N, 14.26; C, 48.27; H, 6.90; Cl, 18.39; S, 8.49.

EXAMPLE 21

2-Methyl-4-(4-cyclopropyl-1-piperazinyl)-7,8-dihydro-6H-thiapyrano[3,2-d]pyrimidine Dihydrochloride The product of Example 17, Step B, was treated with four equivalents of N-cyclopropylpiperazine (Prepared from N,N-bis(β-chloroethyl)p-toluenesulfonamide and cyclopropylamine as reported by J. Mills and C. W. Ryan to Eli Lilly & Co., U.S. Pat. No. 3,342,816, June 1, 1965.) in isoamyl alcohol at 100° C. according to Procedure III. The product was purified by chromatography on silica gel using 5% methanol in chloroform as eluant and converted to the dihydrochloride. Crystallization of that product gave the title compound in 30% yield. The product gave m/e=290 and showed a 200 MHz pmr spectrum that is fully consistent with the assigned structure.

Anal. Calcd for $C_{15}H_{24}Cl_2N_4S$ (363.34): N, 15.42; C, 49.28; H, 6.66; Cl, 19.51; S, 8.82. Found: N, 15.50; C, 49.50; H, 6.38; Cl, 19.27; S, 8.88.

EXAMPLE 22

2-Methyl-4-(4-benzyl-1-piperazinyl-7,8-dihydro-6H-thiapyrano[3,2-d]-pyrimidine Dihydrochloride The product of Example 17, Step B, was treated with four equivalents of N-benzylpiperazine, in isoamyl alcohol at 100° C. according to Procedure III. The product was purified by chromatography on silica gel using 2% methanol in chloroform for elution. The product was converted to the dihydrochloride with 2N HCl and the salt was decolorized with Darco charcoal in aqueous solution. The aqueous solution was concentrated to dryness and the residue was treated with hot ethanol and the mixture was centrifuged. The supernatant ethanol solution was concentrated to dryness giving the title compound as a glass, in 70% yield. The product gave a m/e=340 and the 200 MHz pmr spectrum was fully compatible with the structure designated for the compound.

Anal. Calcd for $C_{19}H_{26}Cl_2N_4S \bullet 0.6C_2H_5OH \bullet 0.8H_2O$ (455.47): N, 12.30; C, 53.26; H, 6.90; Cl, 15.57; S, 7.04. Found: N, 12.18; C, 53.06; H, 6.75; Cl, 15.84; S, 6.56.

EXAMPLE 23

2-Methyl-4-(4-carboethoxy—piperazinyl)-7,8-dihydro-6H-thiapyrano[3,2-d]pyrimidine Hydrochloride The product of Example 17, Step B, was treated with 4 equivalents of ethyl N-piperazinocarboxylate in isoamyl alcohol at 100° C. according to Procedure III. The product was purified by chromatography on silica gel using 5% methanol in chloroform for elution and the product was converted to the dihydrochloride using anhydrous hydrogen chloride in ethanol. The title compound was isolated in 60% yield after crystallization from hot ethanol. The product showed m/e=322 and gave a 200 MHz pmr spectrum that was completely consistent with the structure projected for the compound.

Anal. Calcd for $C_{15}H_{23}ClN_4O_2S$ (358.88): N, 15.62; C, 50.20; H, 6.46; Cl, 9.88; S, 8.93. Found: N, 15.31; C, 50.12; H, 6.36; Cl, 9.68; S, 8.65.

EXAMPLE 24

2-Chloro-7,8-dihydro-6H-thiapyrano[3,2-d]pyrimidine

A mixture of 2,4-dichloro-7,8-dihydro-6H-thiapyrano[3,2-d]pyrimidine (5.0 g, 22.6 mMol), anhydrous sodium acetate (3.7 g, 45.2 mMol), and 10% palladium on carbon (7.5 g) in absolute ethanol (100 ml) was hydrogenated at 3 atmospheres (gauge) with rocking at room temperature. After 2 hours, additional palladium on carbon (3 g) was added and hydrogenation was continued for 3 hours. The reaction mixture was filtered and concentrated in vacuo. The oil was dissolved in 200 ml of dichloromethane, filtered and concentrated to leave 2-chloro-7,8-dihydro-6H-thiapyrano[3,2-d]pyrimidine as an oil (2.85 g, 15.3 mMol, 68%); nmr (CDCl$_3$) δ: 8.24 (1H, s), 3.02 (2H, t), 2.91 (2H, t), 2.20 (2H, m).

EXAMPLE 25

2-Piperazino-7,8-dihydro-6H-thiapyrano[3,2-d]pyrimidine

A mixture of 2-chloro-7,8-dihydro-6H-thiapyrano[3,2-d]pyrimidine (187 mg, 1.00 mMol) and piperazine (344 mg, 4.00 mMol) was heated at 100° C. under nitrogen for 1.5 hours. The cooled mixture was worked up with 5% sodium bicarbonate (25 ml) and chloroform (25 ml). The organic layer was concentrated to an oil which was triturated with diethyl ether to give 2-piperazino-7,8-dihydro-6H-thiapyrano[3,2-d]pyrimidine (118 mg, 0.5 mMol, 50%) as white solid, m.p. 125°–6° C.; nmr (CDCl$_3$) δ: 7.98 (1H, s), 3.67 (4H, t), 2.92 (2H, t), 2.86 (4H, t), 2.71 (2H, t), 2.14 (2H, m); mass spectrum (E.I.): 236 (M+).

A mixture of 2-piperazino-7,8-dihydro-6H-thiapyrano[3,2-d]pyrimidine (71 mg, 0.30 mMol) and maleic acid (69 mg, 0.60 mMol) was dissolved in chloroform, concentrated in vacuo and triturated with ether to leave the dimaleate salt, m.p. 180°–2°.

EXAMPLE 26

2-(N-Methylpiperazino)-7,8-dihydro-6H-thiapyrano[3,2-d]pyrimidine

In the manner described in Example 25, 2-chloro-7,8-dihydro-6H-thiapyrano[3,2-d]pyrimidine (140 mg, 0.75 mMol) and 1-methylpiperazine (400 mg, 4 mMol) were heated to afford 2-(N-methyl-piperazino)-7,8-dihydro-6H-thiapyrano[3,2d]pyrimidine (129 mg, 0.51 mMol, 68%) as an oil.

A portion of the free base thus obtained was converted into the maleate in methanol and recrystallized from MeOH-ether to give the maleate salt with a m.p. of 191°–192° C. Both mass spectra and nmr were consistent with the desired structure.

EXAMPLE 27

2-Chloro-4-methyl-7,8-dihydro-6H-thiapyrano[3,2-d]pyrimidine

To a stirred suspension of methyl triphenylphosphonium bromide (2.2 equiv.) in anhydrous 1,2-dimethoxyethane under dry nitrogen at −30° to −35° C. was added n-butyllithium in hexane (2.2 equiv.); the reaction mixture was stirred for 1 hour, and 2,4-dichloro-7,8-dihydro-6H-thiapyrano[3,2-d]pyrimidine (1 equiv.) in anhydrous 1,2-dimethoxyethane was added.

The mixture was allowed to warm slowly (about 1 hour) to room temperature and then stirred at room temperature for 16 hours. Sodium carbonate (1 equiv.) in water was added to the above solution of the heterocyclic ylide; the mixture was refluxed for 3 hours, evaporated under pressure, and then suspended in chloroform and extracted with dilute aqueous hydrochloric acid, the combined aqueous layers were made alkaline with sodium hydroxide and the resulting mixture was extracted with ether. The combined ether extracts were dried and evaporated, and the product was purified by recrystallization.

EXAMPLE 28

2-Piperazino-4-methyl-7,8-dihydro-6H-thiapyrano[3,2-d]pyrimidine

In the same manner described in Example 25, 2-piperazino-4-methyl-7,8-dihydro-6H-thiapyrano[3,2-d]pyrimidine was prepared from 2-chloro-4-methyl-7,8-dihydro-6H-thiapyrano[3,2-d]pyrimidine and piperazine.

EXAMPLE 29

4-[4-(2-Hydroxyethyl)piperazino]-2-methyl-7,8-dihydro-6H-thiapyrano[3,2-d]pyrimidine maleate A mixture of 201 mg (1.0 mMol) of 2-methyl-4-chloro-7,8-dihydro-6H-thiapyrano[3,2-d]pyrimidine and 520 mg (4.00 mMol) of 2-(2-hydroxyethyl)piperazine was stirred at 105° C. under N$_2$ for 1 hour. The mixture was treated with 10 ml of 5% NaHCO$_3$ and was extracted with 20 ml of chloroform. The solution was dried over magnesium sulfate and concentrated to an oil which was chromatographed over 20 cc of basic alumina with 25 ml fractions of chloroform. The solution was removed in vacuo to leave an oil which was treated with 110 mg (0.95 mMol) of maleic acid in a minimum of methanol. The solution was diluted with 25 ml of diethylether to give 230 mg (0.56 mM) of white solid, m.p. 104°–8° C. NMR (free base in CDCl$_3$) δ: 2.21 (2H, 5°), 2.50 (3H, 1°), 2.64 (6H, m), 2.87 (2H, 3°, thiapyrano ring), 2.95 (2H, 3°, thiapyrano ring), 3.45 (4H, 3°), 3.65 (2H, 3°) mass spectrum (EI): m/E 294 (m+).

Elemental Analysis Calcd for C$_{14}$H$_{22}$N$_4$O$_5$•C$_4$H$_4$O$_4$: C, 52.67; H, 6.38; N, 13.65; S, 7.81. Found: C, 52.13; H, 6.25; N, 12.74; S, 7.39.

EXAMPLE 30

4-(4-Hydroximinopiperidino)-2-methyl-7,8-dihydro-6H-thiapyrano[3,2-d]pyrimidine maleate A mixture of 352 mg (1.75 mMol) of 2-methyl-4-chloro-7,8-dihydro-6H-thiapyrano[3,2-d]pyrimidine, 600 mg (5.25 mMol) of 4-hydroximinopiperidine and 3 ml of isvamyl alcohol was heated at 110° C. for 1 hour under N$_2$. The cooled mixture was concentrated in vacuo, treated with 15 ml of 5% sodium bicarbonate solution, and extracted in 2×20 ml of chloroform. The chloroform was dried over magnesium sulfate and concentrated in vacuo to give 220 mg (0.72 mMol) of a white solid, 4-(4-hydroximinopiperidino)-2-methyl-7,8-6H-thiapyrano[3,2-d]pyrimidine)(b). NMR (CDCl$_3$) δ: 2.17 (2H, 5°) 2.41 (1H, 3°), 2.43 (3H, 1°), 2.72 (2H, 3°), 2.81 (2H, 3°, thiapyrano ring), 2.90 (2H, 1°), 2.91 (2H, 3°, thiapyrano ring), 3.48 (2H, 3°), 3.53 (2H, 3°).

MS (EI): m/e 278 (Mf)

Elemental Analysis Calcd for C$_{13}$H$_{18}$N$_4$O$_5$•H$_2$O: C, 52.68; H, 6.80; N, 18.90; S, 10.82. Found: C, 52.74; H, 6.46; N, 19.05; S, 10.21.

A mixture of 41 mg (0.15 mMol) of the free base and 17 mg (0.15 mMol) of maleic acid was dissolved in a small amount of methanol which was removed in vacuo. The residue was triturated with diethyl ether to leave 58 mg of the title compound as a white solid, m.p. 234–7°.

EXAMPLE 31

4-Methoxyiminopiperidine

A mixture of 7.68 g (50.0 mMol) of 4-piperidone monohydrate hydrochloride and 4.17 g (47.9 mMol) of O-methylhydroxylamine hydrochloride was refluxed in 30 ml of ethanol for 1.5 hours. The mixture was cooled to 35° C. and was diluted with 150 ml of diethyl ether. Cooling gave 5.14 g (31.2 mMol) of 4-methoxyiminopiperidine hydrochloride as fine crystals, m.p. 143° C. (with dec).

A solution of 3.3 g (20.0 mMol) of the hydrochloride was dissolved in 10 ml of H$_2$O and was treated with 20 ml of sodium hydroxide (20.0 mMol) to raise the pH to 8.9. The solution was concentrated in vacuo, dried by concentrating from 50 ml of ethanol and the 50 ml of acetonitrile, and extracted with 125 ml of hot benzene which gave 1.27 g (10.0 mM) of white needles on cooling of the title compound, m.p. 115°-18° C. (trace to 132°). NMR (CDCl$_3$) δ: 2.81 (2H, 3°), 2.95 (2H, 3°), 3.27 (2H, 3°), 3.36 (2H, 3°), 3.85 (3H, 3°).

EXAMPLE 32

4-(4-Methoxyiminopiperidino)-2-methyl-7,8-dihydro-6H-thiapyrano[3,2-d]pyrimidine maleate A mixture of 201 mg (1.0 mMol) of 2-methyl-4-chloro-7,8-dihydro-6H-thiapyrano[3,2-d]pyrimidine and 500 mg (3.91 mMol) of 4-methoxyiminopiperidine was heated at 110° C. under N$_2$ for 2 hours. The mixture was treated with 20 ml of 5% sodium bicarbonate and 30 ml of chloroform. The chloroform was concentrated in vacuo and the remaining oil was chromatographed on 30 cc of basic alumia with chloroform (25 ml fractions). Fraction 2 was concentrated in vacuo to give 63 mg (0.22 mMol) of white solid (2), m.p. 125°-6° C. NMR (CDCl$_3$) δ: 2.20 (2H, 5°), 2.46 (2H, 3°), 2.49 (3H, 1°), 2.72 (2H, 3°), 2.88 (2H, 3°), 2.97 (2H, 3°), 3.49 (2H, 3°), 3.56 (2H, 3°), 3.85 (3H, 1°).

A mixture of 46 mg of the free base and 18 mg of maleic acid was dissolved in a minimum of methanol and concentrated in vacuo. The residue was stirred with 50 ml of diethyl ether which gave a white solid on concentration in vacuo to leave the title compound.

EXAMPLE 33

4-(4-Aminopiperidino)-2-methyl-7,8-dihydro-6H-thiapyrano[3,2-d]pyrimidine

A mixture of 201 mg (1.00 mMol) of 2-methyl-4-chloro-7,8-dihydro-6H-thiapyrano[3,2-d]pyrimidine, 520 mg (3.00 mMol) of 4-aminopiperidine dihydrochloride, (See Emert et al., Chem. Ber. 48, 691 (1915)) 0.84 ml (6.00 mMol) of triethylamine and 4 ml of isoamyl alcohol was stirred at 130° C. for 2 hours under nitrogen. The cooled mixture was concentrated in vacuo, treated with 20 ml of 5% sodium bicarbonate solution and extracted with 2×20 ml of chloroform. The chloroform was dried over magnesium sulfate and concentrated in vacuo to give an oil which was chromatographed on 30 cc of Brinkman E. Merck kiesel gel 60 (70-230mesh) with 50 ml fractions of 1:1-ethylacetate:hexane. Fractions 3 and 4 were combined and concentrated and the residue was dissolved in 1N hydrochloric acid which was concentrated in vacuo to give 95 mg (0.31 mMol) of 4-piperidino-2-methyl-7,8-dihydro-6H-thiapyrano[3,2-d]pyrimidine hydrochloride as a solid, m.p. 157°-60° C. NMR (CDCl$_3$) δ: 1.7 (6H, broad 1°), 2.21 (2H, 5°), 2.49 (3H, 1°), 2.86 (2H, 3°), 2.93 (2H, 3°), 3.36 (4H, narrow multiplet).

Mass spectrum (EI): m/e 249 (M+-1).

Calcd for C$_{13}$H$_{21}$ClN$_3$S: C, 54.43; H, 7.38; N, 14.65; Cl, 12.35. Found: C, 54.06; H, 6.56; N, 14.15; Cl, 12.11.

EXAMPLE 34

2-(β-Methoxyethyl)-4-(4-ethyl-1-piperazinyl)-7,8-dihydro-6H-thiapyrano[3,2-d]pyrimidine dihydrochloride A solution of 2-(β-methoxyethyl)-4-chloro-7,8-dihydro-6H-thiapyrano[3,2d]pyrimidine, the product of Example 12, Step B, in isoamyl alcohol is added dropwise to a hot stirred solution of four equivalents of N-ethylpiperazine in isoamyl alcohol as outlined in Procedure III. The reaction mixture is worked up according to Procedure III yielding the title compound.

EXAMPLE 35

2-(β-Methoxyethyl)-4-(4-n-propyl-1-piperazinyl)-7,8-dihydro-6H-thiapyrano[3,2d]pyrimidine dihydrochloride A mixture of 6 mmoles of 1-n-propylpiperazine dihydrochloride and 12 mmoles of triethylamine in 10 ml of isoamyl alcohol is heated to 100° C. Next, a solution of 1.5 mmoles of 2-(β-methoxyethyl)4-chloro-7,8-dihydro-6H-thiapyrano[3,2-d]pyrimidine from Example 12, Step B in 10 ml of isoamyl alcohol is added dropwise to the hot stirred solution in the course of about 30 minutes. The reaction is allowed to proceed and is worked up in the manner described in Procedure III to yield the title compound.

What is claimed is:

1. A compound having the formula:

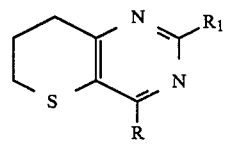

wherein:
R$_1$ is hydrogen, loweralkyl, loweralkenyl of from 2 to 6 carbon atoms; cycloalkyl of from 3 to 6 carbon atoms, phenyl, nitrophenyl, pyridyl phenylloweralkyl, loweralkoxy, loweralkylthio, loweralkoxyloweralkyl or phenylloweralkoxyloweralkyl;

R is

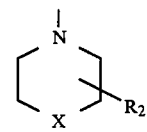

wherein R$_2$ is hydrogen or lower alkyl; X is —CH(NH$_2$), —(C=NOH)—, —(C=NOAlk)— where Alk is loweralkyl or —(N—R$_3$)— where R$_3$ is loweralkenyl of from 3 to 6 carbon atoms, loweralkynyl of from 3 to 6 carbon atoms, cycloalkyl of from 3 to 6 carbon atoms, hydroxyloweralkyl, or loweralkoxycarbonyl.

2. The compound of claim 1 wherein R$_1$ is ethyl, n-propyl, cyclopropyl, or vinyl; and X is N—R$_3$ wherein R$_3$ is loweralkenyl or hydroxyloweralkyl.

3. The compounds of claim 2 wherein R$_3$ is 2-propenyl.

4. The compound of claim 1 which is 2-methyl-4-[4-(2-propenyl)piperazinyl]6H-thiapyrano[3,2-d]pyrimidine.

5. The compound of claim 1 which is 2-methyl-4(4-cyclopropyl piperazinyl)-6H-thiapyrano[3,2d]pyrimidine.

6. A method for lowering the blood glucose levels of diabetics or insulin resistant obese patients which comprises orally administering to such patients an effective amount of a compound of claim 1.

7. An orally administered composition useful for lowering blood glucose levels of diabetics or insulin resistant obese patients which comprises an inert carrier and a compound of claim 1.

* * * * *